(12) United States Patent
Ghiraldi

(10) Patent No.: US 7,428,042 B2
(45) Date of Patent: Sep. 23, 2008

(54) FOOD ANALYZER FOR SELF-PROPELLED FOOD LOADING UNITS, AND RELATIVE OPERATING METHOD

(75) Inventor: Andrea Ghiraldi, Poggio Rusco (IT)

(73) Assignee: Dinamica Generale S.R.L., Poggio Rusco (IT)

( * ) Notice: Subject to any disclaimer, the term of this patent is extended or adjusted under 35 U.S.C. 154(b) by 600 days.

(21) Appl. No.: 11/084,845

(22) Filed: Mar. 18, 2005

(65) Prior Publication Data

US 2005/0223905 A1   Oct. 13, 2005

(30) Foreign Application Priority Data

Mar. 19, 2004   (IT) .......................... BO2004A0160

(51) Int. Cl.
   *G01J 3/00*   (2006.01)
(52) U.S. Cl. ........................... 356/73; 356/300
(58) Field of Classification Search ............. 356/73, 356/300; 56/10.2 R
   See application file for complete search history.

(56) References Cited

U.S. PATENT DOCUMENTS 5,751,421 A   5/1998   Wright et al.
6,421,990 B1 *   7/2002   Ohlemeyer et al. ...... 56/10.2 R
2004/0130714 A1 *   7/2004   Gellerman et al. .......... 356/300

FOREIGN PATENT DOCUMENTS

| EP | 1 053 671 A1 | 11/2000 |
| JP | 02156856 | 6/1990 |
| JP | 04310846 | 11/1992 |
| JP | 2002346483 | 12/2002 |
| WO | WO 01/46678 A2 | 6/2001 |
| WO | WO 03/081188 A2 | 10/2003 |

OTHER PUBLICATIONS

European Search Report for EP 05 10 2191 dated Jun. 7, 2005.

* cited by examiner

*Primary Examiner*—Gregory J Toatley, Jr.
*Assistant Examiner*—Kara E Geisel
(74) *Attorney, Agent, or Firm*—Marcus S. Simon; Graybeal Jackson Haley LLP

(57) ABSTRACT

A food analyzer which can be installed on a self-propelled food loading unit, and which includes an optoelectronic device for determining the spectrum of electromagnetic radiation reflected and/or absorbed by a foodstuff loaded by the self-propelled unit; and a processing unit for determining, as a function of the acquired spectrum of electromagnetic radiation, chemical and physical information relative to the elements in the foodstuff.

32 Claims, 5 Drawing Sheets

FOOD ANALYZER FOR SELF-PROPELLED FOOD LOADING UNITS, AND RELATIVE OPERATING METHOD

PRIORITY CLAIM

This application claims priority from Italian patent application No. BO2004A 000160, filed Mar. 19, 2004, which is incorporated herein by reference.

TECHNICAL FIELD

The present invention relates to a food analyzer for self-propelled food loading units.

More specifically, the present invention relates to a food analyzer which can be installed on a self-propelled food harvesting and/or loading unit, such as a balers, or a pick up balers, or a round balers, or a large rectangular balers, or a mixer wagon, or a shredder-mixer wagon, to which specific reference is made in the following description purely by way of example.

BACKGROUND OF THE INVENTION

As is known, in stock-breeding, improvements to livestock diet are becoming increasingly important to ensure good health of the animal, on the one hand, and, on the other, to improve the quality and yield of directly derived products, such as milk or other dairy products.

At present, the diet of livestock such as cattle is "prescribed" by a specialist, typically an agronomist, who, on the basis of laboratory analyses, determines the nutritional values characteristic of each foodstuff prescribed in the animal's diet.

Once the nutritional values, such as moisture, protein, dry substance, etc., of each foodstuff are established, the agronomist determines, on the basis of the physical and yield conditions of the animal, the correct amount of foodstuffs to be introduced into the animal's diet.

As is known, in many stock-breeding farms and establishments, each foodstuff is measured, and the food ration of each animal is prepared by means of a self-propelled unit, i.e. a loader-mixer wagon typically referred to as a "shredder-mixer wagon", which more or less automatically loads up with each foodstuff according to the weight prescribed in the set diet. More specifically, last-generation loader-mixer wagons are equipped with a weighing system, which determines the weight of the foodstuff loaded instant by instant, and controls loading of the foodstuffs into the wagon according to the set weight in each animal's diet.

Before being finally loaded and distributed, however, the foodstuffs in the animals' diet are often stored in areas or depots where they are exposed for prolonged periods to atmospheric agents, such as rain, which, as is known, seriously affects their properties and nutritional values.

As a result, the diet actually administered to the animal differs considerably from the set diet based on laboratory analysis, thus possibly resulting in an unbalanced diet and, consequently, in poor quality and yield of the associated products. Moreover, variations in the nutritional characteristics of the diet are potentially harmful to the animal itself, which, in the event of a seriously unbalanced diet, may be subjected to such stress as to impair its physical condition.

SUMMARY OF THE INVENTION

It is an object of the present invention to provide a food analyzer which can be installed on a self-propelled loading unit, such as a food loading wagon, and which provides for eliminating the aforementioned drawbacks.

According to the present invention, there is provided a food analyzer, as claimed in the attached claims.

According to the present invention, there is also provided a self-propelled unit, as claimed in the attached claims According to the present invention, there is also provided an operating method of the analyzer, as claimed in the attached claims

BRIEF DESCRIPTION OF THE DRAWINGS

A non-limiting embodiment of the present invention will be described by way of example with reference to the accompanying drawings, in which.

DETAILED DESCRIPTION OF THE INVENTION

Figure 1:
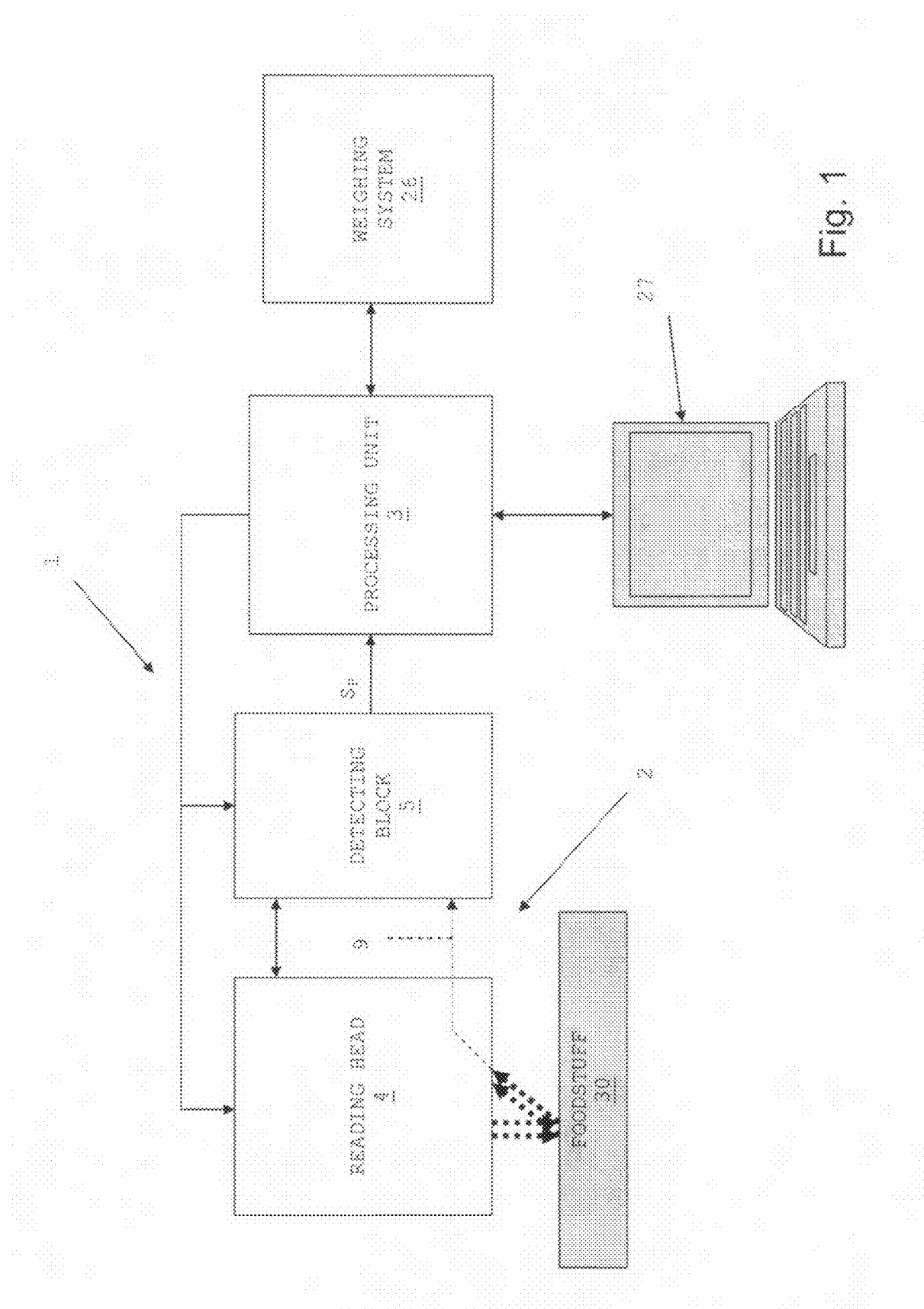
FIG. 1 shows, schematically, a food analyzer for self-propelled food loading units, in accordance with the teachings of the present invention.
Figure 6:
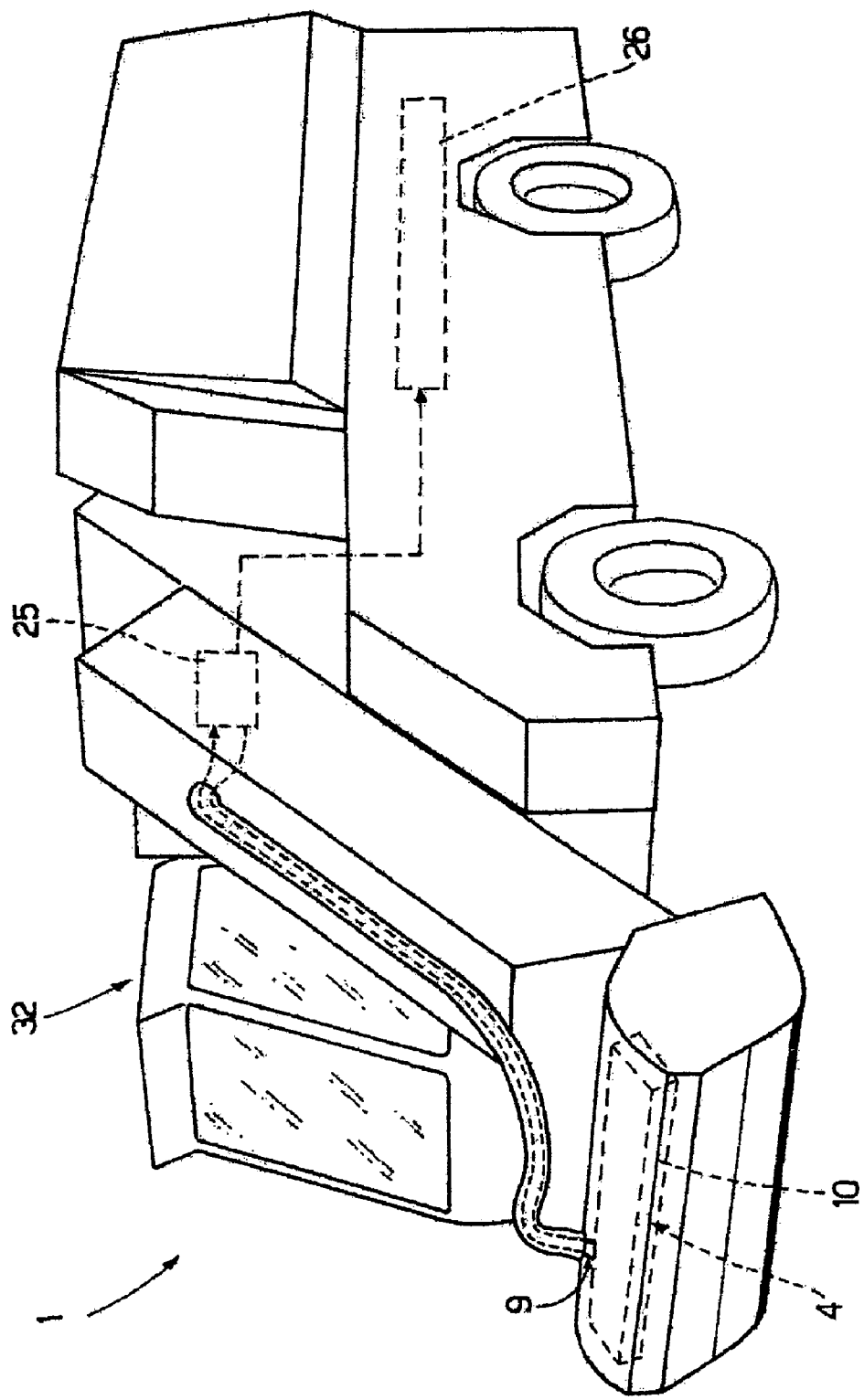
FIG. 6 shows, schematically, a food loading wagon equipped with the FIG. 1 food analyzer.

With reference to FIGS. 1 and 6, number 1 indicates as a whole a food analyzer, preferably for animal food, which can be installed on a self-propelled unit, preferably a food harvesting, loading and distribution wagon 32, e.g. a shredder-mixer wagon, to "optoelectronically" analyze the foodstuff/s loaded by the self-propelled unit, so as to indicate the chemical and physical characteristics of the elements of each foodstuff.

More specifically, the self-propelled unit may comprise a harvesting and/or loading wagon such as a balers, or a pick up balers, or a round balers, or a large rectangular balers, or a mixer wagon, or a shredder-mixer wagon, or any other similar type of wagon, which may be towed, i.e. drawn by another vehicle, such as a tractor (not shown), or may be self-propelled (FIG. 6).

With reference to FIG. 1, analyzer 1 substantially comprises a spectrometer 2, which can be installed in wagon 32 to emit a beam of electromagnetic radiation onto at least one foodstuff 30 inside wagon 32, to supply a spectrum signal $S_P$ coding the spectrum of the electromagnetic radiation reflected by foodstuff 30; and a processing unit 3, which receives and processes spectrum signal $S_P$ to acquire information relative to the chemical elements or compounds contained in the analyzed foodstuff.

More specifically, spectrometer 2 comprises a reading head 4, which is preferably, though not necessarily, installed on the loader of wagon 32 or anywhere else inside the wagon, to emit the beam of electromagnetic radiation onto foodstuff 30 as it is loaded onto wagon 32; and a detecting block 5 for receiving the beam of electromagnetic radiation reflected by foodstuff 30 and supplying spectrum signal $S_P$ coding the spectrum of the electromagnetic radiation reflected by foodstuff 30.

Figure 2:
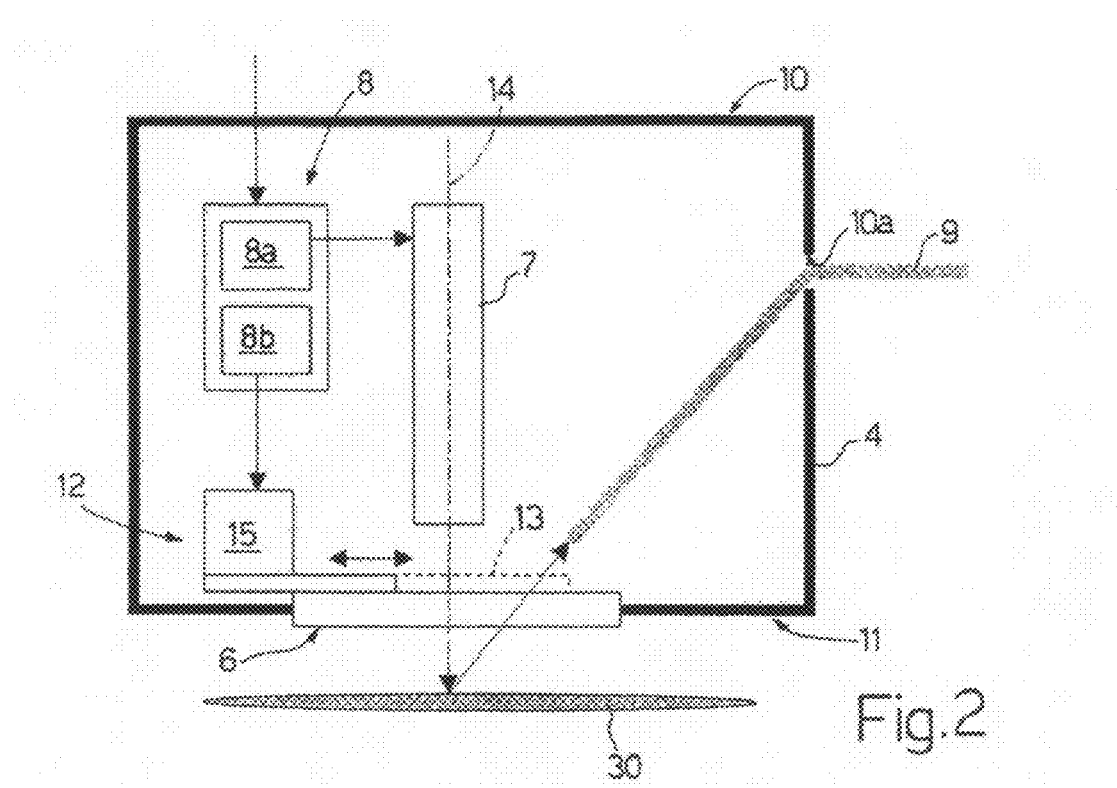
FIG. 2 shows, schematically, a reading head forming part of the FIG. 1 analyzer.

With reference to FIG. 2, reading head 4 comprises an optical assembly 6 positioned with an outer surface preferably, though not necessarily, adjacent to or contacting foodstuff 30 for analysis; a radiation emission source 7 for emitting the beam of electromagnetic radiation through optical assembly 6 onto foodstuff 30 for analysis; an electronic control module 8 for controlling emission source 7 to control emission of the beam of electromagnetic radiation; and an optical conducting element 9 for receiving the beam of electromagnetic radiation reflected by foodstuff 30 and transmitting it to detecting block 5.

In the FIG. 2 example, reading head 4 comprises a protective casing or container 10 made of preferably rigid material, e.g. metal or plastic, and housing: emission source 7, electronic control module 8, optical assembly 6, and a portion of optical conducting element 9.

More specifically, protective casing 10 is preferably sealed to withstand atmospheric agents and so advantageously protect the components inside from water and dust, and is preferably, though not necessarily, located or integrated in the loader of wagon 32, with a bottom lateral wall 11 facing the foodstuff for analysis. More specifically, in the FIG. 2 example, the bottom lateral wall 11 of protective casing 10 has a surface portion made of transparent material, e.g. a glazed surface, which defines optical assembly 6 of reading head 4.

In the absence of the loader on wagon 32, protective casing 10 may obviously be installed anywhere else in wagon 32, so that the glazed surface defining optical assembly 6 faces the foodstuff for analysis.

Moreover, protective casing 10 may obviously be installed anywhere else in balers (not illustrated), so that the glazed surface defining optical assembly 6 faces the foodstuff for analysis.

Emission source 7 may be defined, for example, by a lamp or similar emission device for emitting a beam of electromagnetic radiation in a predetermined direction, preferably, though not necessarily, perpendicular to the plane of the surface portion of transparent material. More specifically, the beam generated by the lamp may be a "light" beam of electromagnetic radiation of a wavelength preferably in the visible and/or nearby infrared spectrum.

In the example shown, optical conducting element 9 is defined by an optical fiber, also indicated 9 hereinafter, which extends from reading head 4 to detecting block 5 to transmit the beam of electromagnetic radiation reflected by foodstuff 30 to detecting block 5. More specifically, optical fiber 9 is positioned with an end portion inside protective casing 10, so that a first end faces the surface portion of transparent material to receive the beam of electromagnetic radiation reflected by foodstuff 30.

In the FIG. 2 example, optical fiber 9 is fitted through an opening or hole 10a formed through a lateral wall of protective casing 10, and extends inside protective casing 10 so as to substantially slope with respect to an axis 14 perpendicular to the surface portion of transparent material, with its first end facing the inner face of the surface portion of transparent material. Optical fiber 9 may conveniently be fitted through opening or hole 10a through a guide (not shown) to keep the longitudinal axis of the inner portion of optical fiber 9 inclined at a given angle, preferably of about 45°, with respect to axis 14, and so conveniently eliminate reception of electromagnetic radiation reflected directly by the surface portion of transparent material.

With reference to FIG. 2, reading head 4 also comprises an automatic calibrating device 12, which cooperates with emission source 7 to calibrate spectrometer 2.

In the FIG. 2 example, automatic calibrating device 12 is housed inside protective casing 10, and comprises a preferably white reference reflecting surface 13; and an electric linear actuator 15, e.g. an electric step motor, which, on command, moves reference reflecting surface 13 from a rest position (shown by the continuous line in FIG. 2), in which reference reflecting surface 13 does not intercept the emitted beam of electromagnetic radiation, and a calibration position (shown by the dash line in FIG. 2), in which reference reflecting surface 13 is so positioned over the surface portion of transparent material as to intercept the emitted beam of electromagnetic radiation and reflect it onto the end of optical fiber 9, which in turn transmits it to detecting block 5.

It should be pointed out that, in use, by receiving and analyzing spectrum signal $S_P$ supplied by detecting block 5 and associated with the beam reflected by reference surface 13, processing unit 3 is able each time and in known manner to set a number of parameters by which to correct the acquired spectrum and so eliminate any errors introduced by the various devices in reading head 4 during emission/acquisition of the beam.

Electronic control module 8 may be defined by an electronic circuit for controlling lamp 7 and activating electric linear actuator 15 during automatic calibration. More specifically, electronic control module 8 comprises a power block 8a defined, for example, by an electronic PWM (Pulse Wave Modulation) circuit for supplying lamp 7 with a current/voltage modulation signal to maintain a constant light intensity of the light beam emitted by lamp 7 throughout the working life of the lamp.

Electronic control module 8 also comprises an actuating block 8b for activating electric linear actuator 15, and which, during automatic calibration, controls movement of reference reflecting surface 13 between the rest position and the calibration position.

Figure 3:
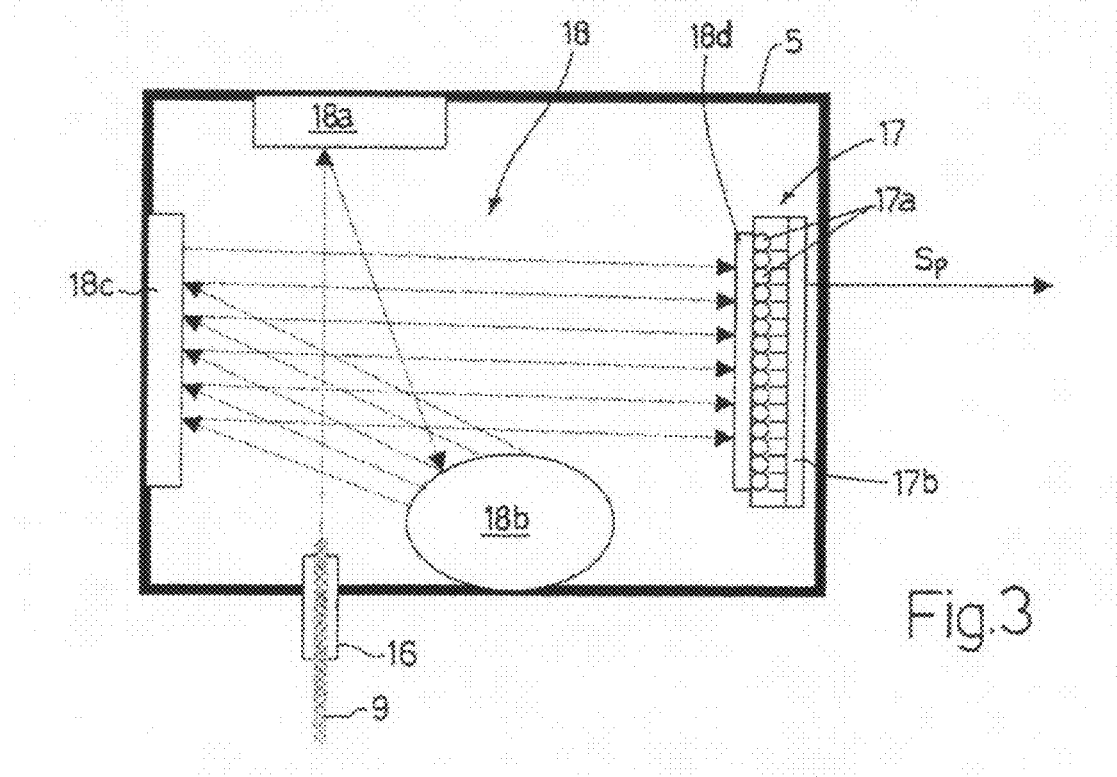
FIG. 3 shows, schematically, a detecting block forming part of the FIG. 1 analyzer.

With reference to FIGS. 1 and 3, detecting block 5 is appropriately connected to the second end of optical fiber 9 to receive, from the optical fiber, the beam of electromagnetic radiation reflected by foodstuff 30, and to convert it into spectrum signal $S_P$ coding the spectrum of frequencies in the incoming beam.

More specifically, with reference to FIG. 3, detecting block 5 substantially comprises a connecting device 16 for optically connecting the second end of optical fiber 9 and detecting block 5; an optical detector 17 for receiving the beam from optical fiber 9 and converting it into spectrum signal $S_P$; and an optical assembly 18 for appropriately conducting to optical detector 17 the beam transmitted by optical fiber 9.

In the FIG. 3 example, optical assembly 18 comprises a collimating lens 18a, a mirror 18b, a prism 18c, and an amplifying lens 18d. In actual use, the beam of electromagnetic radiation conducted by optical fiber 9 is first reflected by collimating lens 18a onto mirror 18b, which deflects it onto prism 18c, with the wavelengths of the radiation in phase with one another. When struck by the beam, prism 18c divides it, as a function of the wavelengths, into a series of radiations, which are directed through amplification lens 18d to optical detector 17, which detects the spectrum of the beam and converts it into spectrum signal $S_P$.

In the FIG. 3 example, optical detector 17 comprises an array of photodiodes 17a; and a conversion circuit 17b, which receives the electric conversion signals supplied by photodiodes 17a, and codes them into spectrum signal $S_P$ containing information relative to the spectrum of the beam reflected by the analyzed foodstuff.

Figure 4:
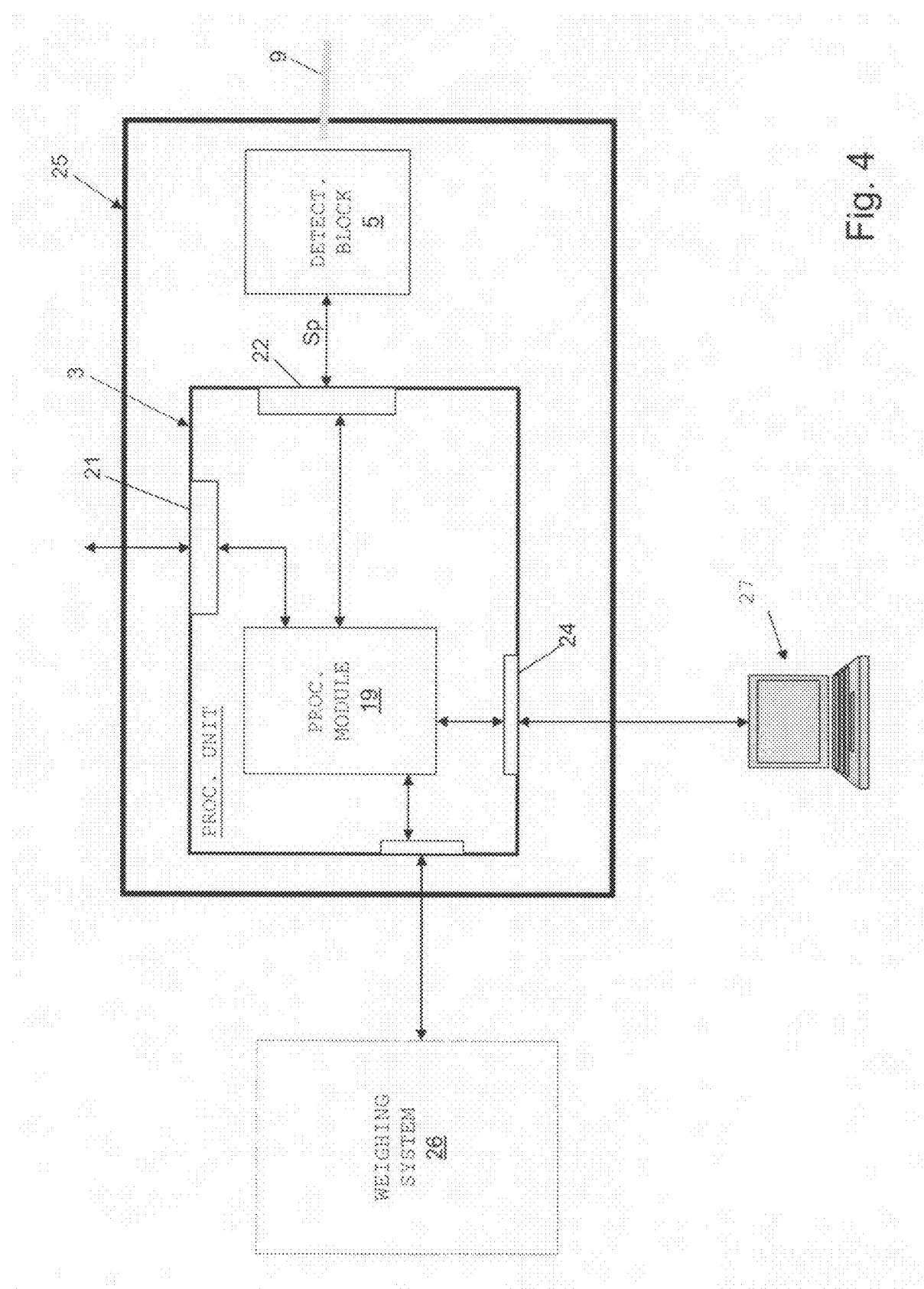
FIG. 4 shows, schematically, a processing unit of the FIG. 1 analyzer.

With reference to FIGS. 1 and 4, processing unit 3 receives spectrum signal $S_P$ from detecting block 5, and processes it to supply information concerning the chemical components or elements characteristic of the loaded foodstuff.

In the FIG. 4 example, processing unit 3 comprises a processing module 19, e.g. a microcontroller, for controlling and coordinating the various operations performed by analyzer 1 to acquire and process the spectrum of the electromagnetic radiation reflected by analyzed foodstuff 30.

More specifically, microcontroller 19 transmits a series of commands to electronic control module 8, via a first communication block 21, to activate emission/reception of the beam and/or automatic calibration, and transmits a series of commands to detecting block 5, via a second communication block 22, to activate conversion of the spectrum of the reflected beam and so receive spectrum signal $S_P$.

Via a third communication block 23, microcontroller 19 also communicates with a weighing system 26 of wagon 32, to which it transmits a signal containing information relative to the chemical components or elements characteristic of the loaded foodstuff. More specifically, weighing system 26 continually determines the weight of the foodstuff loaded onto wagon 32, and controls loading of the foodstuff until the measured weight equals the weight of the foodstuff prescribed in the set diet.

More specifically, in the FIG. 1 and 4 example, weighing system 26 forms part of analyzer 1, and controls loading of the foodstuff onto wagon 32 on the basis of the set diet and as a function of the chemical elements detected by analyzer 1 in the foodstuff loaded onto wagon 32.

More specifically, weighing system 26 determines the weight of the loaded foodstuff, calculates the quantities of chemical elements "loaded" on the basis of the measured weight, compares the actual quantities of the chemical elements in the loaded foodstuff with those prescribed in the set diet, and, as a function of the outcome of the comparison, activates or stops loading of the foodstuff onto wagon 32.

In other words, weighing system 26 controls loading of the foodstuff so that the quantities of the chemical elements in the loaded foodstuff actually correspond to those prescribed in the set diet.

Weighing system 26 therefore provides for updating the weights of the foodstuffs prescribed in the set diet on the basis of the actual quantities of the chemical elements detected by the analyzer in each foodstuff as it is loaded onto wagon 32.

Microcontroller 19 preferably, though not necessarily, also communicates, via a fourth communication block 24, with an external computer, e.g. a personal computer 27, to which it transmits a signal containing information relative to the chemical components or elements characterizing the loaded foodstuff. The information may contain, for example, the concentration and/or weight of each detected chemical element.

The first, second, third, and fourth communication block 21-24 may be defined by respective communication ports for transmitting and receiving data/signals between the devices using a standard, e.g. USB, communication protocol, a serial protocol, or any other similar communication protocol.

In the FIG. 4 and 6 example, processing unit 3 and detecting block 5 are conveniently housed in a single protective casing 25, which is sealed to protect the above devices inside from water and dust, and is preferably, though not necessarily, located in the operator cab of wagon 32.

In a variation not shown, analyzer 1 is defined by a single portable device; in which case, reading head 4, detecting block 5, and processing unit 3, as opposed to being installed separately on wagon 32 may be integrated in a single food analysis device located on wagon 32.

Moreover, in a variation not shown reading head 4, detecting block 5, and processing unit 3, may be integrated in a single food analysis device located on balers.

Figure 5:
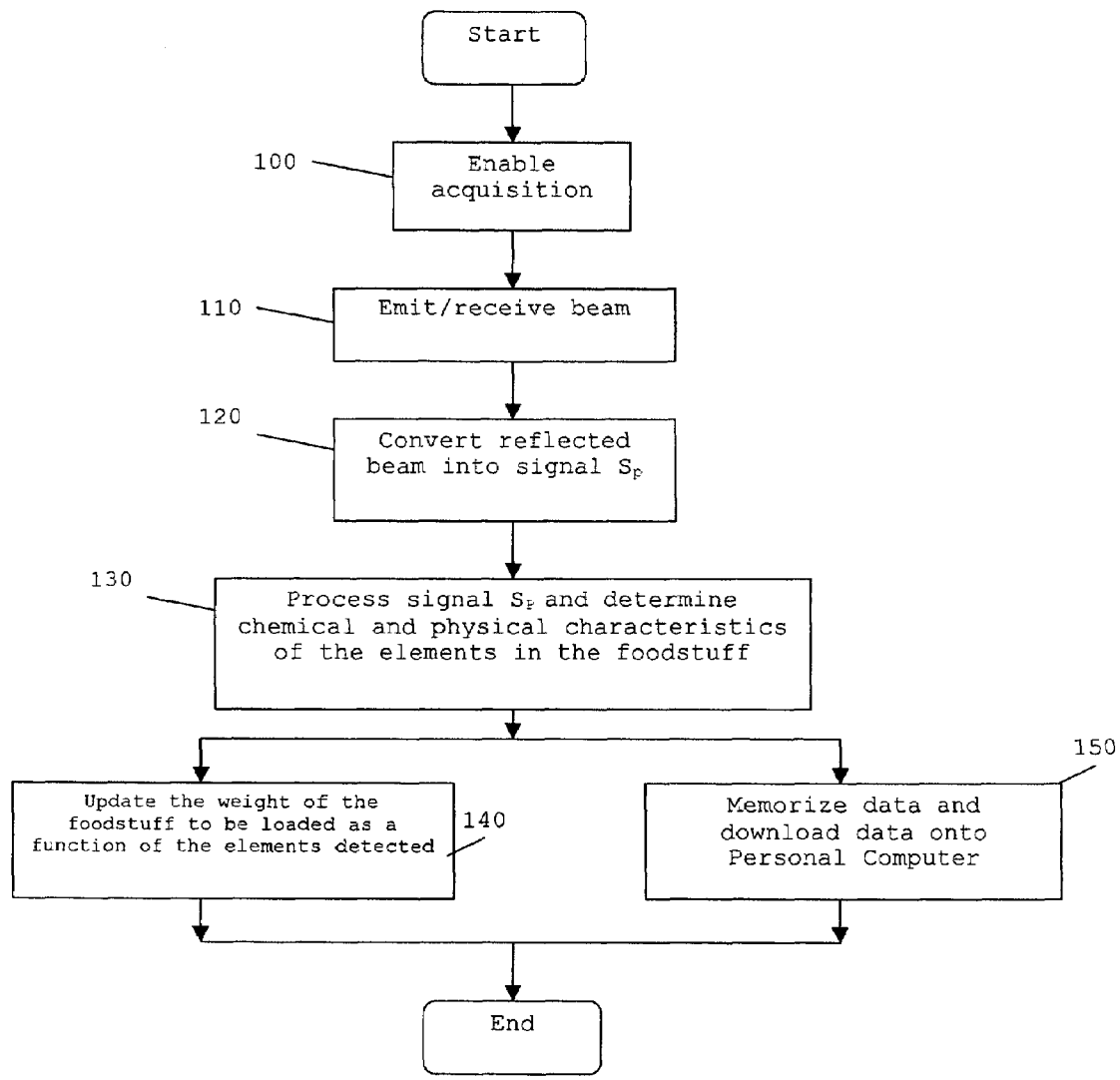
FIG. 5 shows a flow chart of the operations performed by the FIG. 1 analyzer.

FIG. 5 shows a flow chart of the operations performed by analyzer 1.

Analyzer 1 may be activated by a control signal transmitted by weighing system 26 before or as a given foodstuff for analysis prescribed in the set diet is loaded (block 100).

Upon reception of the control signal, processing unit 3 in turn activates reading head 4, which commands emission of the beam of electromagnetic radiation onto foodstuff 30 by lamp 7. The beam of electromagnetic radiation reflected by foodstuff 30 is picked up by optical fiber 9, which transmits it to detecting block 5 (block 110).

The beam of electromagnetic radiation transmitted to detecting block 5 by optical fiber 9 is appropriately conveyed by optical assembly 18, which divides the beam into the various component electromagnetic radiations, which are projected, amplified, to optical detector 17, which, by means of photodiodes 17a, converts them into spectrum signal $S_P$, which is supplied by detecting block 5 to processing unit 3 (block 120).

At this point, microcontroller 19 of processing unit 3 implements a processing algorithm by which information relative to the elements in foodstuff 30 is determined as a function of the spectrum of frequencies in the reflected beam.

It should be pointed out that the processing algorithm implemented by microcontroller 19 to determine the elements is preferably based on analysis of the diffuse reflectance produced by foodstuff 30, which, being a known spectral analysis method, is not described in detail (block 130). In particular, by means of such analysis, processing unit 3 is able to determine the concentration (weight and/or percentages) of elements such as water, dry substance (a measurement complementary to the quantity of water), starch, protein, raw protein (term indicating the quantity of nitrogen), fiber, and various other chemical elements or compounds characterizing the analyzed foodstuff.

At this point, processing unit 3 transmits the information relative to the detected chemical elements to weighing system 26, which controls loading of the foodstuff onto wagon 32 accordingly (block 140).

On receiving information relative to the chemical elements, weighing system 26 can therefore modify the weight of each foodstuff prescribed in the diet as a function of the concentration of the detected elements, so that, once the foodstuff is loaded onto wagon 32 (or loaded on balers), the actual quantity or concentration of each element in the foodstuff satisfies a given relationship with a given threshold. For example, the weighing system may update the weight of hay in the set diet so that the loaded hay contains a given quantity or concentration of water and/or starch and/or protein.

In connection with the above, it should be pointed out that the operating method of the food analyzer according to the present invention and as described above comprises the steps of:

emitting, by means of lamp 7, a beam of electromagnetic radiation onto the foodstuff loaded or to be loaded onto wagon 32;

determining, by means of spectrometer 2, the electromagnetic radiation reflected by the foodstuff, to supply spectrum signal $S_P$ containing the spectrum of the reflected electromagnetic radiation; and acquiring, by means of processing unit 3, chemical and physical information relative to the elements in the loaded foodstuff as a function of the acquired radiation spectrum.

Once the chemical and physical information relative to the elements in the loaded foodstuff is acquired, analyzer 1 determines, by means of weighing system 26, the weight of the foodstuff loaded onto wagon 32, and controls loading of the foodstuff onto wagon 32 as a function of the measured weight and on the basis of the chemical and physical information relative to the elements in the loaded foodstuff.

Once the chemical and physical information relative to the elements in the loaded foodstuff is acquired, analyzer 1 also provides for updating the set weight of the foodstuff to be loaded onto wagon 32 as a function of the measured weight and on the basis of the chemical and physical information relative to the elements in the loaded foodstuff.

Analyzer 1 therefore provides for updating the set foodstuff weights in the diet directly as a function of the basic chemical substances or elements actually contained in the foodstuffs, such as dry substance, starch, protein, fiber, etc., as opposed to solely on the basis of the foodstuffs for loading, i.e. the quantity of hay, silo-stored fodder, corn meal. As such, the chemical elements in the foodstuffs loaded onto wagon 32 (or loaded onto balers) correspond exactly to the quantities prescribed in the set diet.

Weighing system 26 may, of course, display the information relative to the set diet and/or to the detected chemical elements on an operator display or monitor (not shown), and may allow the operator to enter manual commands, e.g. to update diet parameters, by means of a control device, e.g. a keyboard (not shown).

Processing unit 3 also stores the information relative to the chemical elements temporarily for subsequent transmission to the personal computer (block 150), so that the agronomist or operator is informed of the chemical and physical characteristics of the foodstuff as it is being loaded onto wagon 32 (or onto the balers).

Analyzer 1 advantageously provides for real-time analysis of the foodstuffs to be administered, thus enabling variation of the set diet quantities as a function of the actual nutritional values of each foodstuff, with obvious advantages as regards both the health of livestock and the quality and yield of associated products.

Analyzer 1 also provides for a more correct, more accurate diet definition as a function of the basic elements to be administered, as opposed to the weight of food. In other words, diet can be set directly as a function of the amount of water, starch, protein, and dry substance to be administered.

Finally, food analyzer 1 according to the invention may also be installed to advantage on any unit, station or circuit for transporting and distributing animal food, and comprising belt devices or conveyors for transporting and distributing food to individual animals.

Clearly, changes may be made to analyzer 1 as described and illustrated herein without, however, departing from the scope of the present invention.

What is claimed is:

1. A food analyzer which can be installed on a self-propelled food loading unit, comprising:
    optoelectronic means for determining a spectrum of electromagnetic radiation reflected and/or absorbed by at least one foodstuff loaded by the self-propelled unit;
    processing means for determining, as a function of the acquired spectrum of electromagnetic radiation, chemical and physical information about elements in the loaded at least one foodstuff; and
    a weighing system operable to
        measure a weight of the at least one foodstuff loaded onto the self-propelled unit,
        receive the chemical and physical information,
        control loading of the at least one foodstuff onto the self-propelled unit as a function of the measured weight and on the basis of the chemical and physical information, and
        update a set weight of the at least one foodstuff to be loaded onto the self-propelled unit as a function of the measured weight and on the basis of the chemical and physical information.

2. The analyzer as claimed in claim 1, in further comprising:
    wherein the optoelectronic means comprise an emission source for emitting a beam of electromagnetic radiation onto the at least one foodstuff; and
    detecting means for detecting the electromagnetic radiation reflected by the at least one foodstuff, to supply an electric signal containing the spectrum of the reflected said electromagnetic radiation.

3. The analyzer as claimed in claim 2, further comprising:
    wherein the detecting means comprise a spectrum detecting block for converting the reflected electromagnetic radiation into the electric signal; and
    optoelectronic conducting means for detecting the electromagnetic radiation reflected by the at least one foodstuff, and transmitting the electromagnetic radiation to the spectrum detecting block.

4. The analyzer as claimed in claim 3, wherein the spectrum detecting block comprises a number of optoelectronic sensors.

5. The analyzer as claimed in claim 3, wherein the optoelectronic conducting means comprise at least one optical fiber.

6. The analyzer as claimed in claim 5, further comprising:
    an automatic calibrating device which cooperates with the emission source to calibrate emission of the beam of electromagnetic radiation; and
    a control block which controls the emission source to modulates, in a controlled manner, the beam of electromagnetic radiation onto the at least one foodstuff, and which controls the automatic calibrating device during automatic calibration.

7. The analyzer as claimed in claim 3, further comprising:
    at least one optical assembly, and
    a casing housing the emission source and the optoelectronic conducting means, the casing being installable on the self-propelled unit.

8. The analyzer as claimed in claim 7, wherein the optical assembly comprises a flat surface portion of transparent material integrated in the casing and facing the at least one foodstuff to permit emission of the beam of electromagnetic radiation by the emission source outwards of the casing.

9. The analyzer as claimed in claim 8, wherein said the emission source is operable to emit the beam of electromagnetic radiation in a direction substantially perpendicular to the plane of the flat surface portion of transparent material, and that an optical fiber is housed in the casing in a position substantially inclined by a given angle with respect to said plane.

10. The analyzer as claimed in claim 5, further comprising a protective casing housing the processing means, the spectrum detecting block and a portion of the at least one optical fiber; the protective casing being installable on the self-propelled unit.

11. The analyzer as claimed in claim 1, wherein the processing means comprise communication means for communicating to an external processing device the chemical and physical information.

12. A self-propelled food loading unit, comprising a food analyzer as claimed in claim 1.

13. The self-propelled food loading unit as claimed in claim 12, further comprising loading means for loading the at least one foodstuff onto said self-propelled unit; and wherein the weighing system is operable to control loading of the at least foodstuff by the loading means as a function of the chemical and physical information, and as a function of the weight of the at least one foodstuff loaded onto the self-propelled unit.

14. The self-propelled food loading unit as claimed in claim 12, further comprising a balers, pick up balers, round balers, large rectangular balers, mixer wagon, or a shredder-mixer wagon.

15. A method of operating an analyzer for analyzing food loadable onto a self-propelled unit, comprising:

acquiring, by means of optoelectronic means, a spectrum of electromagnetic radiation reflected and/or absorbed by at least one foodstuff loaded onto the self-propelled unit;

determining, by means of processing means and as a function of the acquired spectrum of electromagnetic radiation, chemical and physical information about elements in the loaded at least one foodstuff; and updating a set weight of the at least one foodstuff to be loaded onto the self-propelled unit as a function of a measured weight and on the basis of the chemical and physical information.

16. The method as claimed in claim 15, further comprising:

emitting, by means of an emission source, a beam of electromagnetic radiation onto the at least one foodstuff; and determining, by means of detecting means, electromagnetic radiation reflected by the at least one foodstuff, to supply an electric signal containing the spectrum of the reflected electromagnetic radiation.

17. The method as claimed in claim 15, further comprising:

measuring a weight of the at least one foodstuff loaded onto the self-propelled unit; and controlling loading of the at least one foodstuff onto the self-propelled unit as a function of the measured weight and on the basis of the chemical and physical information.

18. A food analyzer configured for installation on a self-propelled food loading unit, comprising:

an emission device operable to emit a beam of electromagnetic radiation towards at least one foodstuff loaded by the self-propelled unit;

a detector operable to receive electromagnetic radiation from the at least one foodstuff responsive to the at least one foodstuff interacting with the beam of electromagnetic radiation;

a processor operable to determine, as a function of a spectrum of the received electromagnetic radiation, chemical and physical information about elements in the at least one foodstuff; and a weighing system operable to:

measure a weight of the at least one foodstuff loaded onto the self-propelled unit, receive the chemical and physical information control loading of the at least one foodstuff onto the self-propelled unit as a function of the measured weight and on the basis of the chemical and physical information, and update a set weight of the at least one foodstuff to be loaded onto the self-propelled unit as a function of the measured weight and on the basis of the chemical and physical information.

19. The analyzer as claimed in claim 18, further comprising:

wherein the detector is operable to convert the received electromagnetic radiation into an electric signal; and an optical conducting element operable to collect the received electromagnetic radiation, and transmit the collected received electromagnetic radiation to the detector.

20. The analyzer as claimed in claim 19, wherein the detector comprises a number of optoelectronic sensors.

21. The analyzer as claimed in claim 20, wherein the optical conducting element comprises at least one optical fiber.

22. The analyzer as claimed in claim 21, further comprising:

an automatic calibrating device that cooperates with the emission device to calibrate emission of the beam of electromagnetic radiation; and a control block that controls modulation of the beam of electromagnetic radiation emitted from the emission device and the automatic calibrating device during automatic calibration.

23. The analyzer as claimed in claim 19, further comprising:

at least one optical assembly, and a casing housing the emission device and the optoelectronic conducting element, the casing being installable on the self-propelled unit.

24. The analyzer as claimed in claim 23, wherein the optical assembly comprises a flat surface portion of transparent material integrated in the casing and facing the at least one foodstuff to permit emission of the beam of electromagnetic radiation by the emission source outwards of the casing.

25. The analyzer as claimed in claim 24, wherein the emission device is operable to emit the beam of electromagnetic radiation in a direction substantially perpendicular to the plane of the flat surface portion of transparent material, and an optical fiber is housed in the casing in a position substantially inclined by a given angle with respect to the plane.

26. The analyzer as claimed in claim 21, further comprising a protective casing housing the processor and a portion of the at least one optical fiber; the protective casing being installable on the self-propelled unit.

27. The analyzer as claimed in claim 18, wherein the processor comprises a communication block operable to communicate the chemical and physical information to an external computer.

28. A self-propelled food loading unit, comprising a food analyzer as claimed in claim 18.

29. The self-propelled food loading unit as claimed in claim 28, further comprising a loader operable to load the at least one foodstuff onto the self-propelled unit.

30. The self-propelled food loading unit as claimed in claim 29, further comprising balers, pick up balers, round balers, large rectangular balers, a mixer wagon, or a shredder-mixer wagon.

31. A method of operating an analyzer for analyzing food loadable onto a self-propelled unit, comprising:

directing a beam of electromagnetic radiation towards at least one foodstuff loaded by the self-propelled unit;

receiving electromagnetic radiation from the at least one foodstuff loaded responsive to act of directing a beam;

determining, as a function of a spectrum of the received electromagnetic radiation, chemical and physical information about elements in the at least one foodstuff; and updating a set weight of the at least one foodstuff to be loaded onto the self-propelled unit as a function of a measured weight and on the basis of the chemical and physical information.

32. The method as claimed in claim 31, further comprising:

measuring a weight of the at least one foodstuff loaded onto the self-propelled unit; and controlling loading of the at least one foodstuff onto the self-propelled unit as a function of the measured weight and on the basis of the chemical and physical information.

\* \* \* \* \*